United States Patent
Herwig et al.

(10) Patent No.: US 6,861,540 B2
(45) Date of Patent: Mar. 1, 2005

(54) PROCESS FOR THE EPOXIDATION OF CYCLIC ALKENES

(75) Inventors: Jürgen Herwig, Hünxe (DE); Martin Roos, Haltern am See (DE); Georg Oenbrink, Dülmen (DE); Bernd Günzel, Haltern am See (DE); Jörg Lohmar, Dortmund (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/683,047

(22) Filed: Oct. 14, 2003

(65) Prior Publication Data

US 2004/0116722 A1 Jun. 17, 2004

(30) Foreign Application Priority Data

Oct. 11, 2002 (DE) .......................................... 102 47 495

(51) Int. Cl.[7] .............................................. C07D 301/12
(52) U.S. Cl. ........................ 549/531; 549/512; 549/523
(58) Field of Search ................................ 549/512, 523, 549/531

(56) References Cited

U.S. PATENT DOCUMENTS 5,274,140 A    12/1993   Venturello et al.
6,610,864 B2 *  8/2003   Krebs et al. ................. 549/531

FOREIGN PATENT DOCUMENTS

| DE | 30 27 349 | 2/1981 |
|---|---|---|
| EP | 0 987 259 | 3/2000 |
| EP | 1 167 334 | 1/2002 |

OTHER PUBLICATIONS

W.A. Herrmann, et al., Angew. Chem., vol. 103, No. 12, pp. 1706–1709, "Methyltrioxorhenium ALS Katalysator Fuer Die Olefin–Oxidation", 1991.

M. Henschke, Fortschritt–Berichte VD–Verlagl, vol. 3, No. 379, "Dimensionierung Liegender Fluessig–Fluessig–Abscheider Anhand Diskontinuierlicher Absetzversuche", 1995.

* cited by examiner

*Primary Examiner*—Amelia A. Owens
(74) *Attorney, Agent, or Firm*—Oblon, Spivak, McClelland, Maier & Neustadt, P.C.

(57) ABSTRACT

The epoxidation of cyclic, at least monounsaturated alkenes is conducted by a process, which comprises conducting the epoxidation of a cyclic, at least monounsaturated alkene in the presence of an oxidant in a reaction medium that contains at least 1% by weight of the saturated cyclic alkane corresponding to the cyclic, at least monounsaturated alkene. In a preferred embodiment the reaction medium contains at least 2.5% by weight of the saturated cyclic alkane corresponding to the cyclic, at least monounsaturated alkene.

30 Claims, 4 Drawing Sheets

US 6,861,540 B2

PROCESS FOR THE EPOXIDATION OF CYCLIC ALKENES

BACKGROUND OF THE INVENTION

1. Field of the Invention

The present invention relates to a process for the epoxidation of alkenes by catalytic oxidation in the liquid phase. It relates in particular to a process for preparing epoxides by oxidation of alkenes in the liquid phase by means of hydrogen peroxide in the presence of a catalyst system based on a transition metal.

2. Description of the Background

Numerous processes for the epoxidation of alkenes are known, and a wide range of different reaction systems or catalyst systems can be used. The epoxidation of alkenes in a homogeneous, liquid phase by means of organic hydroperoxides in the presence of catalysts based on molybdenum, tungsten or vanadium is employed in industry. However, the preparation of epoxides is accompanied by equivalent or even larger amounts of the alcohol corresponding to the hydroperoxide, and the utilization or recirculation of the alcohol greatly restricts the industrial use of such a process.

For this reason, more direct oxidation processes (epoxidation) of alkenes have been developed.

One such more direct oxidation reaction is epoxidation by means of molecular oxygen using silver catalysts. However, this process has been able to be employed successfully only in the case of ethene; it has not been able to be applied analogously to other alkenes of interest (for example propene).

Another process for direct oxidation of alkenes to epoxides is reaction with hydrogen peroxide. This process has been proposed for various epoxidation reactions especially because of the positive properties of the oxidant in respect of significantly reduced environmental pollution. Since the activity of hydrogen peroxide toward alkenes is only low, in some cases totally absent, it is necessary to employ activating agents, usually organic acids such as formic acid, acetic acid, or the like, in organic solvents. These acids form peracids in situ, and the latter act as the actual reactive epoxidizing agent. These processes, too, do not appear particularly successful, largely because it is difficult to obtain the peracids and because of the instability of the epoxides in an acidic medium, which necessitate rather inconvenient process conditions.

Still another method is the oxidation of alkenes by reaction with highly concentrated hydrogen peroxide in a homogeneous, i.e. exclusively organic, liquid phase in the presence of soluble catalyst systems based on elements of Groups 4, 5 and 6 of the Periodic Table (Ti, V, Mo, W) in combination with elements selected from the group consisting of Pb, Sn, As, Sb, Bi, Hg, and the like. Here too, the results of the process do not permit implementation as an industrial process. This is firstly because the reaction proceeds slowly, and secondly the preparation of the catalyst systems, which generally consist of very complicated organic metal compounds and additionally have to be soluble in the organic reaction medium, is complicated and expensive. Furthermore, the use of highly concentrated hydrogen peroxide (>70%) involves considerable safety risks which cannot easily be overcome in an economical manner.

These processes of the prior art clearly show that the oxidation of alkenes by means of hydrogen peroxide is self-contradictory because the best working conditions in respect of the catalyst system and hydrogen peroxide involve an aqueous, acidic medium while the factors of the oxidation reaction itself and the stability of the epoxide are favored in a neutral organic medium. For this reason, further processes for the epoxidation of alkenes using hydrogen peroxide have been developed, in which either an improved catalyst system based on $TiO_2/SiO_2$ in an aqueous phase with addition of primary or secondary alcohols (see EP 0 987 259 A1) or a two phase system containing a catalyst comprising tungstic acid, a quaternary ammonium salt and a phosphorous compound (for example DE 30 27 349) is used.

In the case of alkenes whose epoxides are not hydrolysislabile and in which the olefinic double bond is not sterically hindered (for example, cyclic at least monounsaturated alkenes), the known epoxidation reaction using hydrogen peroxide and a tungsten catalyst is the most economical alternative.

For the epoxidation reaction by means of hydrogen peroxide to proceed sufficiently quickly, a phase transfer catalyst (for example, ALIOUAT® 336 (tricaprylylmethylammonium chloride)) is usually used in the case of very lipophilic alkenes (for example cyclododecene)(Angew. Chem. (1991), 103(12), 1706–9). However, the desired strong acceleration of the epoxidation by means of the phase transfer catalyst leads to the phases being significantly more difficult to separate after the reaction because of emulsion formation; the corresponding settling times increase greatly. In addition, the organic phase usually remains very turbid after the separation. To achieve virtually complete phase separation, it is necessary to use either phase separators having a very large volume or suitable centrifuges.

The increased settling times in this process greatly reduce its attractiveness for continuous, industrial-scale use. In particular, the process can usually not be implemented at all in existing plants because of space problems caused by the need for larger phase separators. The use of centrifuges is of little interest in view of the power costs and the maintenance requirement due to moving parts.

In quite general terms, it can be said that settling times of less than 2 minutes are industrially desirable. On the other hand, if the settling times are more than 4 minutes, an industrial-scale continuous process is difficult to operate economically.

DE 30 27 349 describes a process for the epoxidation of alkenes using hydrogen peroxide, a tungsten compound, a phosphorous compound and a phase transfer catalyst. In this process, solvents such as alkanes or cycloalkanes are absolutely necessary. These solvents are always added to the reaction mixture in relatively large amounts and generally serve either to dissolve a solid, and thus cause it to react, or improve the reaction conditions, for example in order to achieve better heat removal.

However, the dilution of starting materials with nonreactive substances, for example solvents, is undesirable since, firstly, the dilution leads to a decrease in the spacetime yield and secondly a further separation operation after the reaction is necessary.

SUMMARY OF THE INVENTION

Accordingly, one object of the present invention is to provide a process for the epoxidation of alkenes which can be operated continuously, leads to industrially acceptable settling times of the heterogeneous catalyst/reaction mixture and ensures a sufficiently high space-time yield of epoxide, so that it can be implemented for large-scale manufacture of appropriate epoxides.

Another object of the invention is to provide a process that enables the epoxidation of alkenes to be conducted in existing plants without relatively major modifications having to be made to the plants.

Briefly, these objects and other objects of the present invention as hereinafter will become more readily apparent can be achieved by a process for the epoxidation of cyclic, at least monounsaturated alkenes in the presence of an oxidant, by conducting the oxidation of a cyclic, at least monounsaturated alkene in a reaction mixture containing at least 1% by weight of the corresponding saturated alkane.

In a particularly preferred embodiment of the reaction, the reaction mixture contains at least 2.5% by weight of the alkane corresponding to the cyclic alkene used.

BRIEF DESCRIPTION OF THE DRAWINGS

A greater understanding of the invention in its various embodiments can be ascertained from a consideration of the several drawings of the application, wherein.

DETAILED DESCRIPTION OF THE PREFERRED EMBODIMENTS

Figure 1:
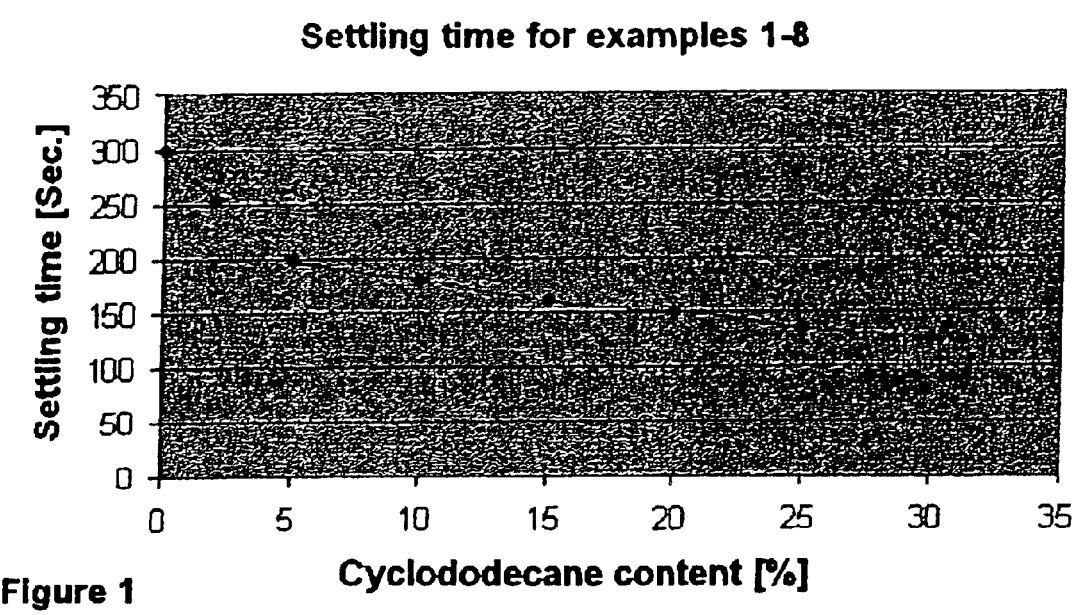
FIG. 1 is a graph of the settling times obtained in the experiments of Examples 1–8.

Throughout the application, the expression "% by weight" means the proportion by weight expressed as a percentage of each component, based on the epoxide.

The discovery of the invention is surprising in that the presence of the alkane corresponding to the olefin employed leads, even in small amounts, to a considerable shortening of the settling times and thus to an overall more economical process.

In contrast to the processes of the prior art which use a phase transfer catalyst, the process of the invention leads to settling times of less than two minutes for the heterogeneous mixture of catalyst and product obtained at the end of the oxidation reaction. For the purposes of the present invention, the settling time is the time after which the phases have completely separated. The phase separation is, for the purposes of providing a clear definition, regarded as complete when the last droplet layer covers only half of the phase interface while the other half can be seen as a clear interface free of dispersion droplets (see: "Dimensionierung liegender Flussig-Flussig-Abscheider anhand diskontinuierlicher Absetzversuche", Dipl. Ing. Martin Henschke, VDI-Verlag, Dusseldorf, 1995).

Furthermore, only the alkane corresponding to the alkene used as starter material is added in the process of the invention.

Even when the upper limit of the corresponding alkane is not itself critical for reducing the settling time, preference is given to using only a small amount of the corresponding alkane to achieve the object of the invention, in general not more than 10% by weight, in particular to ensure an acceptable space-time yield. According to the invention, the corresponding alkane does not function as a solvent. In a particularly preferred embodiment of the present invention, the amounts are, however, so small that the space-time yield of the epoxidation is reduced only insignificantly.

A further, likewise preferred form of the process of the invention is that the heterogeneous process is conducted continuously.

Suitable oxidants for the reaction include all those compounds that are known to those skilled in the art, in particular peroxo compounds. A particularly preferred oxidant is hydrogen peroxide.

If a phase transfer catalyst is necessary to achieve improved reaction conditions, the use or the presence of a catalyst system consisting of or comprising at least one metal of Groups 4, 5 and 6 of the Periodic Table of the Elements is preferred according to the invention. Further constituents of the catalyst system can be phosphoric acid and at least one tertiary amine and/or quaternary ammonium salt. However, it is also possible to use mixtures of these catalyst systems depending on the desired reaction conditions. When such a catalyst system is used, preference is given to adding phosphoric acid and at least one quaternary ammonium salt to the reaction mixture in order to achieve optimal reaction conditions.

The catalyst used in the process of the invention is preferably a metal of Group 4, 5 or 6 of the Periodic Table which can be used in metallic form or in the form of a complex in which the metal has the oxidation state 0 or is present in a variable oxidation state. Particular preference is given to molybdenum, tungsten, vanadium, chromium and titanium.

Among the inorganic derivatives of these elements, it is possible to use the oxides, the mixed oxides, the hydroxides, oxo acids, heteropolyacids, their salts and esters, the salts which are derived from hydrogen acids and from inorganic oxo acids and organic carboxylic or sulfonic acids which have no more than 20 carbon atoms and whose anions are stable under the reaction conditions.

Suitable examples of appropriate catalysts include molybdenum, tungsten, chromium, vanadium, titanium, the carbonylated metals $Mo(CO)_6$, $W(CO)_6$, the oxides $MoO_2$, $Mo_2O_5$, $Mo_2O_3$, $MoO_3$, $WO_2$, $W_2O_5$, $WO_6$, $CrO_2$, $Cr_2O_3$, $CrO_3$, $VO_2$, $V_2O_5$, $ZrO_2$, $TiO$, $TiO_2$, $Ti_2O_3$, $NbO_2$, $Nb_2O_3$, $Nb_3O_5$, and sulfides $MoS_2$, $MoS_3$, $MoS_4$, $Mo_2S_3$, $Mo_2S_5$, the oxyxhlorides of molybdenum, tungsten, chromium, vanadium, zirconium, titanium; the fluorides, chlorides, bromides, iodides, nitrates, sulfates, phosphates, pyrophosphates, polyphosphates, borates, carbonates, formates, octanoates, dodecanoates, naphthenates, stearates, oxalates, succinates, glutarates, adipates, benzoates, phthalates, benzenesulfonates of molybdenum, tungsten, titanium, chromium, zirconium, vanadium; complexes such as acetylacetonate and phthalocyanine; molybdic, tungstic, vanadic, chromic acids, the corresponding heteropolyacids such as phosphomolybdic, phosphotungstic, arsenmolybdic, arsentungstic acids and also all alkali metal or alkaline earth metal salts of these acids.

In a particularly preferred embodiment of the present invention, a tungsten catalyst combined with phosphoric acid is used. The tungsten compound is preferably used in a concentration of from 0.01 to 0.5 mol %, based on the alkene.

The amount of phosphoric acid employed usually ranges from 0.1 to 5 mol %, based on the molar amount of tungsten used.

The quaternary ammonium salts used have the formula

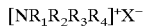

$[NR_1R_2R_3R_4]^+X^-$ where $R_1, R_2, R_3$ and $R_4$ are, independently of one another, linear or branched alkyl chains having from 1 to 20 carbon atoms or aryl groups having from 6 to 10 atoms. The alkyl or aryl groups may, if desired, be substituted by further organic groups or atoms, for example, halogens. $X^-$ is a counterion for the ammonium ion, for example, chloride, bromide, fluoride, iodide, hydrogensulfate, acetate, propionate, or formate.

The tertiary amines have 3 alkyl radicals which may be identical or different and have a total of at least 18 carbon atoms.

In general, preference is given to the use of a homogeneous catalyst. However, it is also possible to use a heterogeneous catalyst in which the catalytically active constituents have been applied in a manner known per se to a support material, for example, aluminum, oxide, silicon dioxide, aluminum silicate, zeolites or suitable polymers.

In the process claimed, the best results have been obtained using a catalyst described in DE 30 27 349 (U.S. Pat. No. 5,274,140). This catalyst comprises a first component composed of at least one element or at least one of its inorganic, organic or organometallic derivatives from the group consisting of W, Mo, V, preferably W, which can be converted in situ and under the reaction conditions into a catalytically active compound.

A particularly useful system comprises 0.2 mol % of sodium tungstate based on cycloalkene, 0.2 mol % of phase transfer catalyst trioctylmethylammonium chloride based on cylcoalkene, 0.1 mol % of phosphoric acid based on cycloalkene and the amount of sulfuric acid which results in a pH of 3.

In a further, likewise preferred embodiment, the reaction mixture comprises at least two liquid phases. Of these, one phase is an aqueous phase in which the hydrogen peroxide is dissolved. This eliminates the use of polar solvents and the associated decrease in the space-time yield and also the increased separation effort.

In a further, preferred embodiment, the pH should be kept constant during the reaction. This can be achieved by means of automatic pH regulation. According to the invention, a favorable pH range is from 2 to 6. The reaction is particularly preferably conducted at a pH of from 2.5 to 4.

As cyclic, at least monounsaturated alkene, it is possible to use all appropriate compounds.

These alkenes can, if desired, be substituted by functional groups which are stable in the reaction medium, for example, hydroxy, chloro, fluoro, bromo, iodo, nitro, alkoxy, amino, carbonyl, acid, ester, amide or nitrile groups.

However, they can also be multiply unsaturated, for example, dienes or trienes in conjugated or non-conjugated form.

The process of the invention is particularly useful for the epoxidation of cyclic, at least monounsaturated alkenes having from 8 to 20 carbon atoms in the ring. In this context, particular mention may be made of cyclooctene, cyclooctadiene, cyclododecene, cyclododecadiene, cyclododecatriene, dicyclopentadiene and cyclododecene. Such alkenes having more than nine carbon atoms, in particular, can be reacted in a significantly better space-time yield compared to processes of the prior art.

A very particularly preferred aspect of the process is its use for the preparation of cyclic epoxyalkanes, in particular 1,2-epoxycyclododecane.

For the purposes of the present invention, the alkane corresponding to the cyclic, at least monounsaturated alkene that is employed is the cyclic, saturated organic compound having the same number of carbon atoms. The corresponding compounds are then selected, for example, from the group consisting of cyclooctane, cyclododecane and dicyclopentane.

The continuous process of the invention can be conducted in one or more reactors. An example is a cascade-like reaction employing a plurality of stages is described in EP 1 167 334 A2. In this disclosure, the reaction mixture is introduced into the first reaction zone and then passes through a plurality of downstream reaction zones until the product-containing mixture is finally discharged from the last reaction zone. The individual reaction zones may be present in different reactors or be integrated into one reactor.

A particularly preferred embodiment of the process of the invention which uses a phase transfer catalyst comprises metering the starting mixture of alkene and the corresponding alkane together with the quaternary ammonium salt into a first reactor. Hydrogen peroxide containing phosphoric acid and the tungsten-based catalyst described in DE 30 27 349 (U.S. Pat. No. 5,274,140) is metered into this reactor in an amount corresponding to the molar amount of alkene. The hydrogen peroxide can be 20 % above or below this amount. After a particular fill level in the first reactor, corresponding to a particular residence time, has been reached, the solution is conveyed continuously either via an overflow or by means of a pump to a further reactor. If desired, a small amount of hydrogen peroxide without catalyst and phosphoric acid is metered into this second reactor. After a particular fill level in the second reactor, corresponding to a particular residence time, has been reached, the solution is conveyed continuously either via an overflow or by means of a pump to a further reactor. If desired, a small amount of hydrogen peroxide without catalyst and phosphoric acid is metered into this third reactor. This form of the reactor cascade can be made-up from 2 to 8 stages. These stages can also be integrated into one reactor in which the plurality of stages is achieved by means of appropriate internals.

The hydrogen peroxide can be divided among the individual reactors depending on the desired conversion. The hydrogen peroxide used is commercial hydrogen peroxide having concentrations ranging from 10 to 70% of hydrogen peroxide in water.

After the reaction has ended and phase separation is complete, the tungsten can be extracted from the organic phase by single-stage or multistage extraction with water which may, if appropriate, contain basic additives such as sodium carbonate, sodium hydrogen carbonate or sodium hydroxide. The alkane can then be removed by distillation together with residual unreacted alkene. From the bottoms of this distillation, the pure epoxide is isolated by fine distillation. The pretreatment acts as purification before the distillation and thus reduces the formation of byproducts.

The temperature of the reaction can range from 50 to 120° C. Preference is given to temperatures ranging from 70 to 100° C.

The reaction is preferably carried out under protective gas such as hydrogen, argon, carbon dioxide, or the like.

Having generally described this invention, a further understanding can be obtained by reference to certain specific examples which are provided herein for purposes of illustration only and are not intended to be limiting unless otherwise specified.

EXAMPLE 1

Comparative Example

Figure 2:
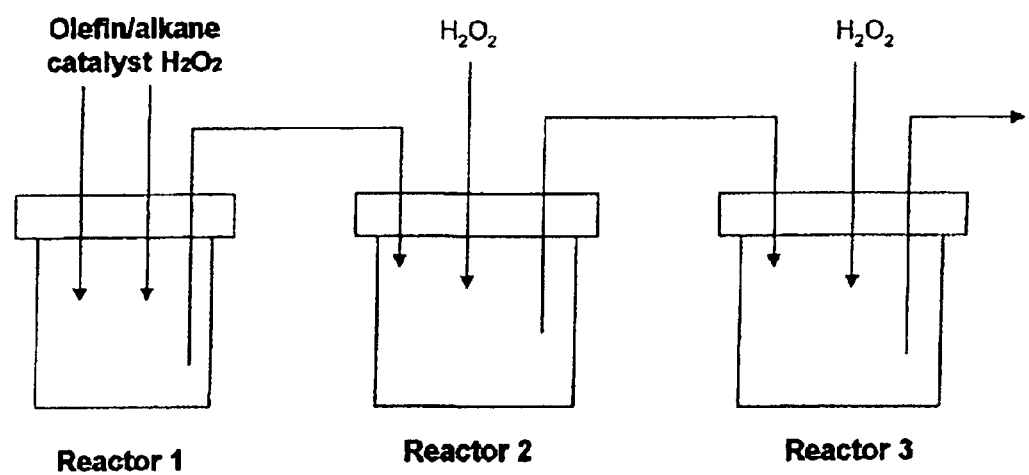
FIG. 2 illustrates an embodiment of the present invention in which the epoxidation of a olefin in the presence of a catalyst occurs in several reactors.
Figure 3:
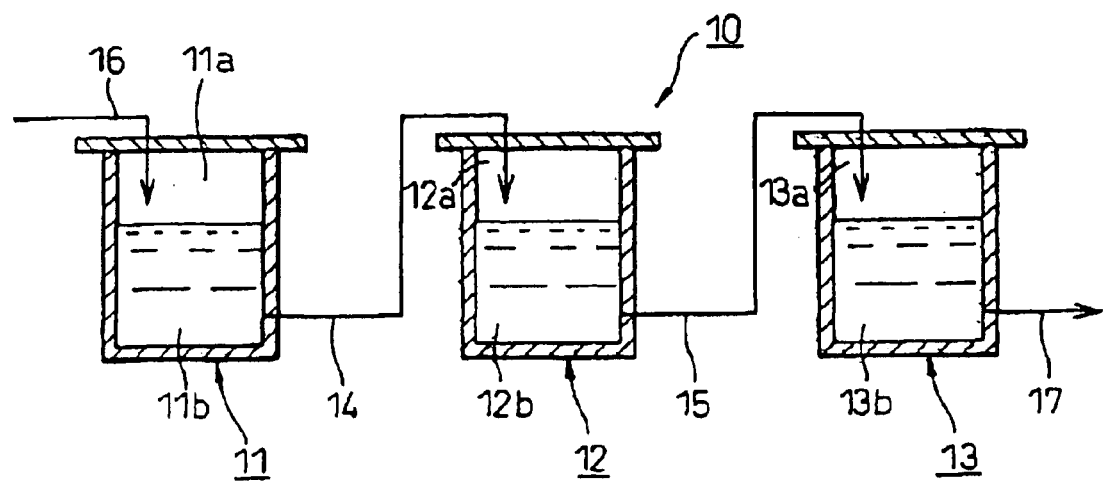
FIG. 3 shows a sequence of three reactors of a first vessel 11, a middle vessel 12 and a last vessel 13, which respectively provide reaction regions separated from each other. The reaction vessels 11, 12 and 13 are connected to each other in series through conduits 14 and 15. The first vessel 11 is connected at a top portion 11a to a feed line 16 which feeds a liquid mixture for reaction to the first vessel 11. Conduit 14 connects the bottom 11b of vessel 11 in fluid connection to the top 12a of middle vessel 12. Similarly, conduit 15 connects the bottom 12b of vessel 12 in fluid connection to the top 13a of middle vessel 13. Discharge of liquid material from the system occurs through conduit 17. The reaction vessels may be completely closed and may be completely filled with the liquid reaction mixture. One or more of the reactors may be sealed with an inert gas, if desired. One or more of the conduits is (are) provided with a liquid transporting means such as a pump.
Figure 4:
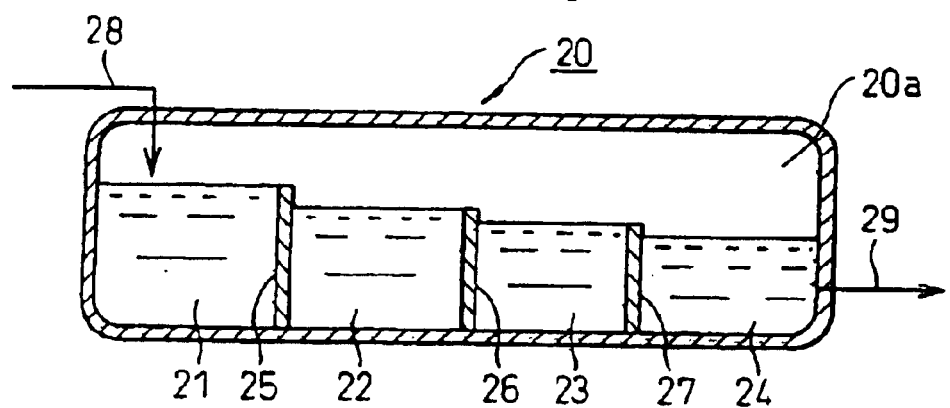
FIG. 4 shows another embodiment of a sequence of reaction zones in which a closed reactor housing 20 is subdivided by partitions 25, 26 and 27 into a plurality of reaction chambers identified as 21, 22, 23 and 24 which form reactions zones. Connected to the first chamber 21 is a feed line 28 which feeds a liquid mixture for reaction to the first chamber 21. The partitions are of unequal height so that the top of the first chamber is higher than the top of the second chamber 22, which in turn is higher than the top of the third chamber 23, which in turn is higher than the top of the fourth chamber 24. The liquid reaction mixture into the reactor housing flows successively from the first chamber 21 through chambers 22, 23 and 24 by the flow of liquid over partitions 25, 26 and 27. Ultimately, reaction mixture is discharged from the apparatus through conduit 29. If desired, the reactor housing may be placed under the atmosphere of an inert gas. Further, if desired, each of partitions 25 to 27 may have at least one hole therein to allow reaction mixture to pass through the chambers at a total flow rate lower than the feed rate of reaction mixture.
Figure 5:
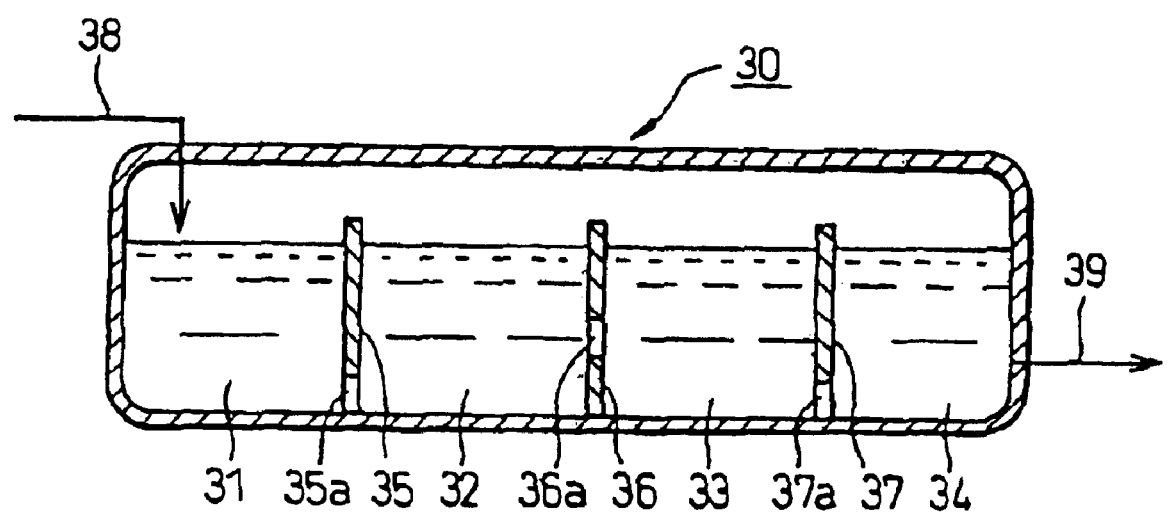
FIG. 5 shows still another embodiment of a sequence of reaction zones in which a closed reactor housing 30 is subdivided by partitions 35, 36 and 37 into a plurality of reaction chambers identified as 31, 32, 33 and 34 which form reactions zones. Each of the partitions has a through hole therein identified as 35a, 36a and 37a which provides fluid communication between reaction chambers. Alternatively, the partitions may be formed of perforated plates. The liquid reaction mixture flows into the reactor housing into the first reaction chamber 31 through conduit 38 and then successively to reaction chambers 32, 33 and 34. Ultimately, reaction mixture is discharged from the apparatus through conduit 39. In the reaction housing, the partitions may be of the same or different height as long as each reaction has a satisfactory capacity for liquid reaction mixture. Any desired number of two or more reaction chambers may be employed.

In an apparatus analogous to that shown in FIG. 2, 249 g of cyclododecene (1.5 mol), 0.99 g of sodium tungstate, 0.59 g of phosphoric acid, 14 g of water, 1.2 g of Aliquat 336 (Cognis) and 10.2 g of hydrogen peroxide were placed in reactor 1 and brought to a pH of 3 by addition of sulfuric acid. The mixture was then heated to 90° C. and 102 g of 50% strength of hydrogen peroxide solution were metered in over a period of 2 hours. A cyclododecene conversion of about 90% was achieved in reactor 1. The volume was about 300 ml. From then on, 2.7 ml/min of a mixture of cyclododecene with 0.2 mol % of Aliquat 336 and 0.73 m/min of a solution of 0.94% of sodium tungstate, 0.56% of phosphoric acid and 98.5% of hydrogen peroxide (50% strength) were metered in continuously over a period of 4 hours. The mixture flowed continuously over an overflow and into reactor 2 which likewise had a volume of 400 ml and was operated at 90° C. After 4 hours of continuous operation, the conversion in reactor 3 was 99.6%.

After the reaction, the settling time for the mixture in reactor 3 was determined. The settling time is the time after which the aqueous phase had settled to such an extent that the two-phase layer at the edge of the reactor was less than 1 mm. The settling time was monitored every 15 seconds. The determination of the settling time was repeated twice and a mean was calculated. The results are shown in Table 1.

EXAMPLE 2

Example According to the Invention

The experiment was conducted by a method analogous to that of Example 1, except that 2% of cyclododecane, based on cyclododecene, was added to the starting materials. The results are shown in Table 1.

EXAMPLE 3

Example According to the Invention

The experiment was conducted by a method analogous to that of Example 1, except that 5% of cyclododecane, based on cyclododecene, was added to the starting material. The results are shown in Table 1.

EXAMPLE 4

Example According to the Invention

The experiment was conducted by a method analogous to that of Example 1, except that 10% of cyclododecane, based on cyclododecene, was added to the starting material. The results are shown in Table 1.

EXAMPLE 5

Example According to the Invention

The experiment was conducted by a method analogous to that of Example 1, except that 15% of cyclododecane, based on cyclododecene, was added to the starting material. The results are shown in Table 1.

EXAMPLE 6

Example According to the Invention

The experiment was conducted by a method analogous to that of Example 1, except that 20% of cyclododecane, based on cyclododecene, was added to the starting material. The results are shown in Table 1.

EXAMPLE 7

Example According to the Invention

The experiment was conducted by a method analogous to that of Example 1, except that 25% of cyclododecane, based on cyclododecene, was added to the starting material.

EXAMPLE 8

Example According to the Invention

The experiment was conducted by a method analogous to that of Example 1, except that 30% of cyclododecane, based on cyclododecene, was added to the starting material.

TABLE 1

| Example No. | Cyclododecane content [% by weight] | Settling time [seconds] |
|---|---|---|
| 1 (comparison) | 0 | 300 |
| 2 | 2 | 255 |
| 3 | 5 | 200 |
| 4 | 10 | 180 |
| 5 | 15 | 160 |
| 6 | 20 | 150 |
| 7 | 25 | 135 |
| 8 | 30 | 125 |

FIG. 1 is a graph of the settling times presented in Table 1 versus cyclododecane content of the experiments of Examples 1–8. It is clear that even at 2% by weight of cyclododecane, the settling time is significantly reduced from 300 seconds to 255 seconds. In the presence of 5% by weight alkane, the settling times decreases to 200 seconds which is ⅔rds of the original settling time. Thus the present invention makes possible industrial phase separation using the phase separators of the present invention.

German priority application Serial Number 10247495.8 filed Oct. 11, 2002, is hereby incorporated by reference into the present application.

Obviously, numerous modifications and variations of the present invention are possible in light of the above teachings. It is therefore to be understood that within the scope of the appended claims, the invention may be practiced otherwise than as specifically described herein.

What is claimed as new and is intended to be secured by Letters Patent is:

1. A process for the epoxidation of cyclic, at least monounsaturated alkenes, which comprises:
   conducting the epoxidation of a cyclic, at least monounsaturated alkene in the presence of an oxidant in a reaction medium that contains at least 1% by weight of the saturated cyclic alkane corresponding to the cyclic, at least monounsaturated alkene.

2. A process for the epoxidation of cyclic, at least monounsaturated alkenes, which comprises:
   conducting the epoxidation of a cyclic, at least monounsaturated alkene in the presence of an oxidant in a reaction medium that contains at least 2.5% by weight of the saturated cyclic alkane corresponding to the cyclic, at least monounsaturated alkene.

3. The process as claimed in claim 1, wherein the heterogeneous reaction is conducted continuously.

4. The process as claimed in claim 2, wherein the heterogeneous reaction is conducted continuously.

5. The process as claimed in claim 1, wherein the oxidant is hydrogen peroxide.

6. The process as claimed in claim 2, wherein the oxidant is hydrogen peroxide.

7. The process as claimed in claim 1, which comprises conducting the reaction in the presence of a catalyst consisting of at least one metal of Group 4, 5 or 6 of the Periodic Table of the Elements.

8. The process as claimed in claim 2, which comprises conducting the reaction in the presence of a catalyst consisting of at least one metal of Group 4, 5 or 6 of the Periodic Table of the Elements.

9. The process as claimed in claim 1, wherein the reaction mixture comprises at least two liquid phases.

10. The process as claimed in claim 2, wherein the reaction mixture comprises at least two liquid phases.

11. The process as claimed in claim 1, wherein the reaction mixture comprises at least one phase transfer catalyst and phosphoric acid.

12. The process as claimed in claim 2, wherein the reaction mixture comprises at least one phase transfer catalyst and phosphoric acid.

13. The process as claimed in claim 1, wherein the phase transfer catalyst comprises at least one tertiary amine and/or a quaternary ammonium salt.

14. The process as claimed in claim 12, wherein the phase transfer catalyst comprises at least one tertiary amine and/or a quaternary ammonium salt.

15. The process as claimed in claim 1, wherein the pH of the reaction mixture is kept in the range from 2 to 6.

16. The process as claimed in claim 2, wherein the pH of the reaction mixture is kept in the range from 2 to 6.

17. The process as claimed in claim 15, wherein the pH of the reaction mixture is kept in the range from 2.5 to 4.

18. The process as claimed in claim 16, wherein the pH of the reaction mixture is kept in the range from 2.5 to 4.

19. The process as claimed in claim 1, wherein the cyclic, at least monounsaturated, alkene has from 8 to 20 carbon atoms in the ring.

20. The process as claimed in claim 2, wherein the cyclic, at least monounsaturated, alkene has from 8 to 20 carbon atoms in the ring.

21. The process as claimed in claim 1, wherein the product is a cyclic epoxyalkane.

22. The process as claimed in claim 2, wherein the product is a cyclic epoxyalkane.

23. The process as claimed in claim 21, wherein the cyclic epoxyalkane is 1,2-epoxycyclododecane.

24. The process as claimed in claim 22, wherein the cyclic epoxyalkane is 1,2-epoxycyclododecane.

25. The process as claimed in claim 13, wherein the wherein the quaternary ammonium salt has the formula:

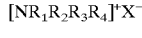

$[NR_1R_2R_3R_4]^+X^-$ wherein $R_1, R_2, R_3$ and $R_4$ each, independently of one another, is a linear or branched, optionally substituted alkyl chain having from 1 to 20 carbon atoms or an optionally substituted aryl group having from 6 to 10 atoms and $X^-$ is a counterion which is chloride, bromide, fluoride, iodide, hydrogensulfate, acetate, propionate or formate.

26. The process as claimed in claim 14, wherein the wherein the quaternary ammonium salt has the formula:

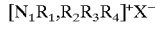

$[N_1R_1,R_2R_3R_4]^+X^-$ wherein $R_1, R_2, R_3$ and $R_4$ each, independently of one another, is a linear or branched, optionally substituted alkyl chain having from 1 to 20 carbon atoms or an optionally substituted aryl group having from 6 to 10 atoms and $X^-$ is a counterion which is chloride, bromide, fluoride, iodide, hydrogensulfate, acetate, propionate or formate.

27. The process as claimed in claim 13, wherein the catalyst is molybdenum, tungsten, chromium, vanadium or titanium metal, $Mo(CO)_6$, $W(CO)_6$, $MoO_2$, $Mo_2O_5$, $Mo_2O_3$, $MoO_3$, $WO_2$, $W_2O_5$, $WO_6$, $CrO_2$, $Cr_2O_3$, $CrO_3$, $VO_2$, $V_2O_5$, $ZrO_2$, $TiO$, $TiO_2$, $Ti_2O_3$, $NbO_2$, $Nb_2O_3$, $Nb_3O_5$, $MoS_2$, $MoS_3$, $MoS_4$, $Mo_2S_3$, $Mo_2S_5$, an oxychloride of molybdenum, tungsten chromium, vanadium, zirconium, titanium; a fluoride, chloride, bromide, iodide, nitrate, sulfate, phosphate, pyrophosphates polyphosphate, borate, carbonate, formate, octanoate, dodecanoate, naphthenate, stearate, oxalate, succinate, glutarate, adipate, benzoate, phthalate or a benzenesulfonate of molybdenum, tungsten, titanium, chromium, zirconium or vanadium; an acetylacetonate or phthalocyanine complex of molybdenum, tungsten, chromium, vanadium or titanium; molybdic, tungstic, vanadic or chromic acid; phosphomolybdic, phosphotungstic, arsenmolybdic or arsentungstic acid or the alkali metal or alkaline earth metal salts of these acids.

28. The process as claimed in claim 14, wherein the catalyst is molybdenum, tungsten, chromium, vanadium or titanium metal, $Mo(CO)_6$, $W(CO)_6$, $MoO_2$, $Mo_2O_5$, $Mo_2O_3$, $MoO_3$, $WO_2$, $W_2O_5$, $WO_6$, $CrO_2$, $Cr_2O_3$, $CrO_3$, $VO_2$, $V_2O_5$, $ZrO_2$, $TiO$, $TiO_2$, $Ti_2O_3$, $NbO_2$, $Nb_2O_3$, $Nb_3O_5$, $MoS_2$, $MoS_3$, $MoS_4$, $Mo_2S_3$, $Mo_2S_5$, an oxychloride of molybdenum, tungsten, chromium, vanadium, zirconium, titanium; a fluoride, chloride, bromide, iodide, nitrate, sulfate, phosphate, pyrophosphate, polyphosphate, borate, carbonate, formate, octanoate, dodecanoate, naphthenate, stearate, oxalate, succinate, glutarate, adipate, benzoate, phthalate or a benzenesulfonate of molybdenum, tungsten, titanium, chromium, zirconium or vanadium; an acetylacetonate or phthalocyanine complex of molybdenum, tungsten, chromium, vanadium or titanium; molybdic, tungstic, vanadic or chromic acid; phosphomolybdic, phosphotungstic, arsenmolybdic or arsentungstic acid or the alkali metal or alkaline earth metal salts of these acids.

29. The process as claimed in claim 1, wherein the reaction is conducted at a temperature ranging from 50 to 120° C.

30. The process as claimed in claim 2, wherein the reaction is conducted at a temperature ranging from 50 to 120° C.

* * * * *